United States Patent
Cranner et al.

(10) Patent No.: US 8,399,032 B2
(45) Date of Patent: Mar. 19, 2013

(54) BRUISE AMELIORATION COMPOSITION AND METHOD OF USE

(75) Inventors: Bruce A. Cranner, Mandeville, LA (US); Anne-Marie T. Karp, New Orleans, LA (US)

(73) Assignee: Dr. Holmquist Healthcare, L.L.C., New Orleans, LA (US)

( * ) Notice: Subject to any disclaimer, the term of this patent is extended or adjusted under 35 U.S.C. 154(b) by 0 days.

(21) Appl. No.: 13/029,551

(22) Filed: Feb. 17, 2011

(65) Prior Publication Data

US 2011/0136900 A1      Jun. 9, 2011

Related U.S. Application Data

(60) Division of application No. 12/248,155, filed on Oct. 9, 2008, which is a continuation-in-part of application No. 11/441,878, filed on May 26, 2006, now abandoned.

(51) Int. Cl.
| | |
|---|---|
| *A61K 31/736* | (2006.01) |
| *A61K 36/785* | (2006.01) |
| *A61K 36/53* | (2006.01) |
| *A61K 36/00* | (2006.01) |

(52) U.S. Cl. ...... 424/735; 424/745; 424/725; 424/78.03

(58) Field of Classification Search .................. None
See application file for complete search history.

(56) References Cited

FOREIGN PATENT DOCUMENTS

JP         55079318 A    *   6/1980

OTHER PUBLICATIONS

"All about peppermint oil" at (www.allgreenrx.com/peppermint.html).*
USPTO OA mailed Mar. 1, 2011 in connection with U.S. Appl. No. 12/248,155.

* cited by examiner

*Primary Examiner* — Christopher R. Tate
*Assistant Examiner* — Deborah A. Davis
(74) *Attorney, Agent, or Firm* — Ladas & Parry LLP

(57) ABSTRACT

A bruise amelioration composition that can be applied for one hour to an affected site, such as a bruise, contusion or blister, in the form of a gel, liquid or adhesive bandage. The composition includes at least 40% by weight of glycerin and at least 2% by weight of primrose oil. Preferably, the composition includes a fragrance, such as peach oil and marjoram and 1% to 10% by weight of vitamins A, C, D, E and K.

20 Claims, No Drawings

BRUISE AMELIORATION COMPOSITION AND METHOD OF USE

CROSS-REFERENCE TO RELATED APPLICATIONS

The present application is a divisional application of U.S. Ser. No. 12/248,155, filed Oct. 9, 2008, and titled, "Bruise Amelioration Composition and Method of Use," which is a continuation-in-part application of U.S. Ser. No. 11/441,878, filed May 26, 2006 now abandoned, and titled, "Bruise Amelioration Composition and Method of Use." The contents of U.S. Ser. No. 12/248,155 and U.S. Ser. No. 11/441,878 are expressly incorporated by reference into the present application.

FIELD OF THE INVENTION

The present invention relates to topical compositions and, more particularly, to a bruise amelioration composition for speedy healing and reduction of discoloration of bruising skin.

BACKGROUND OF THE INVENTION

It is known to use glycerin as a topical application in liquid form to reduce bruising and swelling in human skin. The glycerin prevents discoloration of a bruise and reduces swelling and the pain associated with swelling, if it is applied immediately to an affected area, and the affected area is kept saturated for approximately one hour. It is further known to use this method of bruise amelioration on human skin even where the affected area is abraded. It is also known to use glycerin to reduce and/or eliminate blisters on human feet.

Nelson Homquist, MD, who we credit with developing this human bruise amelioration method, theorized that glycerin is hydrophilic and is absorbed into damaged tissue in advance of blood and other fluid products of ecchymosis. Where so absorbed, the glycerin serves to displace such blood and other fluids and release them into the blood stream thereby leaving the affected area clear (little or no discoloration characteristic of a bruise) with little swelling.

While this human bruise amelioration method (hereinafter, the Homquist Bruise Treatment) is satisfactory, we nevertheless sought to improve upon both the speed and healing quality of the existing compound and method. Compounding glycerin with certain other ingredients (for example, primrose oil) results in an improved bruise amelioration compound and method. Applying the composition in gel, liquid or cream form or in any topical time-release delivery system will speed the healing process. We speculate that the Homquist Bruise Treatment, as well as our improved bruise amelioration method, will achieve similar results in mammals and other warm-blooded animals (such as birds).

SUMMARY OF THE INVENTION

Broadly, a bruise amelioration composition is provided comprising: at least 40% by weight of glycerin and, at least 2% by weight of primrose oil. Another bruise amelioration composition is provided that comprises at least 85% by weight of glycerin and, at least 2% by weight of primrose oil. Yet another bruise amelioration composition is provided that comprises 90 to 95% by weight of glycerin and, at least 2% by weight of primrose oil. Still yet another bruise amelioration composition is provided that comprises at least 95% by weight of glycerin and, at least 2% by weight of primrose oil. Even yet another bruise amelioration composition comprises 85-95% by weight of glycerin, and 2% by weight of primrose oil. Still yet another bruise amelioration composition is provided that comprises 80-95% by weight of glycerin, and 2% by weight of an oil rich in Vitamin C. Yet another bruise amelioration composition is provided that comprises 90-95% by weight of glycerin, and 2% by weight of an oil rich in Vitamin C. These compositions also may include: 1% by weight of peach oil; trace amounts of marjoram; and 1% to 10% by weight of vitamins A, C, D, E and K. These compositions may include 1% by weight of peach oil; trace amounts of marioram; and 1% to 10% of at least one ingredient selected from the group consisting of vitamins A, C, D, E and K. One preferred composition contains 40-45% by weight of glycerin. Another preferred composition contains 90% to 95% by weight of glycerin.

The present invention further contemplates forming the composition in gel or cream form or any topical time-release delivery system.

The present invention further contemplates forming the composition in liquid form.

The present invention further contemplates forming the composition carried in an bandage or other dressing to dispense and retain a dosage of the bruise amelioration composition at the affected site.

In view of the above, an object of the present invention is to provide a bruise amelioration composition that is more effective in the treatment of a bruise or contusion than previously available treatments.

A further object of the present invention is to provide a bruise amelioration composition that is more effective on blisters than previously available treatments.

In view of the above, a feature of the present invention is to provide a bruise amelioration composition that is relatively simple to manufacture.

Another feature of the present invention is to provide a bruise amelioration composition that is simple to use and apply to an affected site.

A still further feature of the present invention is to provide a bruise amelioration composition that has a relatively short response time.

A still further feature of the present invention is to provide a bruise amelioration composition that has a pleasant odor.

A still further feature of the present invention is to provide a bruise amelioration composition that is effective for both humans and other animals.

A still further feature of the present invention is to provide a bruise amelioration composition for humans and other warm-blooded animals of all ages.

A still further feature of the present invention is to provide a bruise amelioration composition which is comprised of non-toxic ingredients.

A still further feature of the present invention is to provide a bruise amelioration composition that can be applied to all exterior parts of the human dermis.

The above and other objects and features of the present invention will become apparent from the description of the example given herein and the appended claims.

DESCRIPTION OF THE EXAMPLE

Referring now to the present invention, the bruise amelioration composition is intended to be applied topically to an affected skin site, contusion site or bruise site (hereinafter referred to as the "affected site"). A contusion is an injury, such as without limitation from a blow with or from a blunt instrument, blunt article or hand, in which the subsurface dermal tissue is injured but the dermis is not broken. The affected site can also include blisters, open cuts and abrasions.

In this example, the formula for the bruise amelioration composition is set forth in the table below.

TABLE

| Ingredient | % by Weight |
|---|---|
| Glycerin | 40-45% |
| Primrose Oil | 2 |
| Peach Oil | 1 |
| Marjoram | trace amt. |
| Vitamins A, C, D, E and K | 2 |

The above ingredients are combined at room temperature. A gel, liquid or cream form, or topical time-release form, of the composition may be made as is known in the art. In fact, any delivery system known to topically treat a bruise, contusion or blister can be used. While not wishing to be bound by theory, peach oil, a natural fruit oil which is an excellent source of natural vitamin C, is carried into the dermal tissue with glycerin where it is absorbed into the cells. This absorption speeds the healing process. Primrose oil softens the skin and also contains naturally occurring vitamins. The oils add a pleasing scent, especially when added with marjoram. Marjoram is an herb which has been used for bruise amelioration. Vitamins A, C, D, E and K each promote and accelerate the healing of damaged tissue. We speculate, as did Dr. Homquist, that the glycerin displaces blood and other fluids of an affected site and releases them into the blood stream thereby leaving the affected area clear (little or no discoloration characteristic of a bruise) with little swelling.

In lieu of peach oil and/or marjoram, another fragrance may be substituted (including, for example, shea butter, lavender, olive oil and other naturally occurring oils and fragrances).

The method of using the bruise amelioration composition includes applying the composition to the affected site as soon as possible after the injury, for a duration of about one hour. We speculate, as did Dr. Homquist, that it is important for the application of glycerin to preempt the natural process of ecchymosis. Our experience has demonstrated that the optimal duration of treatment is about one hour when commenced promptly after injury.

In gel, liquid or cream form, the bruise amelioration composition is viscous, so that when applied, the composition will tend to remain adhered to the affected site. The composition (gel, liquid or cream form) will keep the affected site moist and leach into the injured subsurface dermal tissue of the affected site. The composition should remain on the affected site for at least about one hour.

The bruise amelioration composition described herein may be carried in a bandage or dressing (including adhesive bandages, patches, hydrogel bandages or island dressings) that can be affixed to the affected area of skin to retain the composition in contact with the affected area. The dosage of the bruise amelioration composition carried by the bandage or dressing may be in the form of a gel, liquid or cream. The bandage or dressing may be made available in different sizes to accommodate various affected site sizes.

In liquid form, the bruise amelioration composition can be applied under a bandage or adhesive bandage by saturating a pad of the bandage or adhesive bandage to be applied to the affected site with the composition. For small impacts or blisters, the liquid form of the bruise amelioration composition can be applied to a cotton ball or gauze pad and held in direct contact with the affected site for at least one hour.

The embodiment of the bruise amelioration composition and method described herein in detail, for exemplary purposes, is subject to many different variations in structure, design, application and methodology. Many varying and different embodiments may be made within the scope of the inventive concepts taught herein, and many modifications may be made in the embodiment detailed herein in accordance with the descriptive requirements of the law. Accordingly, it will be understood that the description of this embodiment is not intended to limit the invention, but is intended to cover all modifications falling within the spirit and scope of the invention as expressed in the appended claims.

What is claimed is:

1. A method of treating a skin contusion, the method comprising:
applying a compound comprising 40-45% by weight of glycerin and 2% by weight of an oil rich in vitamin C to the skin contusion; and
maintaining the compound on the skin contusion for about one hour.

2. The method of claim 1, wherein maintaining occurs immediately after the skin contusion arises.

3. The method of claim 1, further comprising:
saturating a pad of a bandage with the composition.

4. The method of claim 3, further comprising:
affixing the bandage onto an affected site of the skin contusion.

5. The method of claim 1, wherein a form of the composition comprises a gel.

6. The method of claim 1, wherein a form of the composition comprises a topical time-release form.

7. The method of claim 3, wherein the bandage is selected from the group consisting of adhesive bandage, patch, hydrogel bandage, and island dressing.

8. The method of claim 1, wherein the compound further comprises 1% by weight of peach oil.

9. The method of claim 1, wherein the compound further comprises a trace amount of marjoram.

10. The method of claim 1, wherein the compound further comprises 2% by weight vitamins A, C, D, E and K.

11. A method of treating a skin contusion, the method comprising:
applying a compound comprising 80-95% by weight of glycerin and 2% by weight of an oil rich in vitamin C to the skin contusion; and
maintaining the compound on the skin contusion for about one hour.

12. The method of claim 11, further comprising:
saturating a pad of a bandage with the composition.

13. The method of claim 12, further comprising:
affixing the bandage onto an affected site of the skin contusion.

14. The method of claim 11, wherein the composition comprises a gel.

15. The method of claim 11, wherein the compound further comprises 1% by weight of peach oil, and a trace amount of marjoram.

16. The method of claim 11, wherein the compound further comprises 2% by weight vitamins A, C, D, E and K.

17. A method of treating a skin contusion, the method comprising:
saturating a pad of a bandage with the composition comprising 80-95% by weight of glycerin and 2% by weight of an oil rich in vitamin C to the skin contusion;

applying the compound saturated on the pad of the bandage to the skin contusion;

affixing the bandage onto an affected site of the skin contusion; and maintaining the compound on the skin contusion for about one hour.

18. The method of claim 17, wherein the compound comprises a gel.

19. The method of claim 17, wherein the compound further comprises 1% by weight of peach oil.

20. The method of claim 17, wherein the compound further comprises 2% by weight vitamins A, C, D, E and K.

* * * * *